United States Patent [19]
de la Chapelle et al.

[11] Patent Number: 5,871,925
[45] Date of Patent: Feb. 16, 1999

[54] TUMOR CLASSIFICATION AS INDICATION OF HEREDITARY NON-POLYPOSIS COLORECTAL CARCINOMA

[75] Inventors: Albert de la Chapelle, Helsinki, Finland; Bert Vogelstein; Kenneth W. Kinzler, both of Baltimore, Md.

[73] Assignee: The Johns Hopkins University, Baltimore, Md.

[21] Appl. No.: 799,940

[22] Filed: Feb. 13, 1997

Related U.S. Application Data

[62] Division of Ser. No. 452,536, May 30, 1995, which is a division of Ser. No. 56,546, May 5, 1993, Pat. No. 5,492,808.

[51] Int. Cl.⁶ .............................. C12Q 1/68; C12P 19/34
[52] U.S. Cl. ................................................ 435/6; 435/91.2
[58] Field of Search ........................................ 435/6, 91.2

[56] References Cited

U.S. PATENT DOCUMENTS

| | | |
|---|---|---|
| 4,666,828 | 5/1987 | Gusella . |
| 5,098,823 | 3/1992 | Bodmer et al. . |
| 5,380,645 | 1/1995 | Vogelstein ................................. 435/6 |
| 5,492,808 | 2/1996 | De La Chapelle et al. ................ 435/6 |
| 5,578,450 | 11/1996 | Thibodeau et al. ......................... 435/6 |

FOREIGN PATENT DOCUMENTS

| | | |
|---|---|---|
| 0390324 | 10/1990 | European Pat. Off. . |
| 2680520 | 2/1993 | France . |

OTHER PUBLICATIONS

Vogelstein et al., *Science* 244, 207–211 (1989).
Caskey et al., *Science* 256, 784–789 (May 8, 1992).
Peinado et al., *Proc. natl. Acad. Sci. USA* 89, 10065–10069 (Nov. 1992).
Mandel, *Nature Genet.* 4, 8–9 (May 1993).
Aaltonen et al., *Science* 260, 812–816 (May 7, 1993).
Pelteriaki et al., *Science* 260, 810–812 (May 7, 1993).
Thibodeau et al., *Science*, 260, 816–819 (May 7, 1993).
Ionov et al., *Nature* 363, 558–561 (Jun. 10, 1993).
Risinger et al., *Cancer Res.* 53, 5100–5103 (Nov. 1993).
Han et al., *Cancer Res.* 53, 5087–5089 (Nov. 1993).
Parsons et al., *Cell* 75, 1227–1236 (Dec. 17, 1993).
Weissenbach, et al., "A Second–Generation Linkage Map of the Human Genome," *Nature*, 359:794–801.
Weber, et al., "Abundant Class of Human DNA Polymorphisms Which Can Be Typed Using the Polymerase Chain Reaction," *Am. J. Hum. Genet.*, 44:388–396, 1989.
Peltomäki, et al., "Evidence Supporting Exclusion of the DCC Gene and a Portion of Chromosome 18q as the Locus for Susceptibility to Hereditary Nonpolyposis Colorectal Carcinoma in Five Kindreds," *Cancer Research*, 51:4135–4140, 1991.
Peltomäki, et al., "Evidence that the MCC–APC Gene Region in 5q21 is not the Site for Susceptibility to Hereditary Nonpolyposis Colorectal Carcinoma", *Cancer Research*, 52:4530–4533, 1992.
Lynch et al., Hereditary Nonpolyposis Colorectal Cancer (Lynch Syndromes I and II), *Cancer* 56(4):939–951 (1985).
Moen et al., "Scc–1 a Novel Colon Cancer Susceptibility Gene in the Mouse: Linkage to CD44 (Ly–24, Pgp–1) on Chromosome 2", *Oncogene* 7:563–566 (1992).

*Primary Examiner*—Kenneth R. Horlick
*Attorney, Agent, or Firm*—Banner & Witcoff, Ltd.

[57] ABSTRACT

Markers on chromosome 2 are associated with cancer predisposition, as shown by linkage analysis, in a significant fraction of families with a history of colon and other cancers. Tumors from these patients progressed through the same series of accumulated mutations in oncogenes and tumor suppressor genes found in non-familial cases, but showed no losses of heterozygosity for the linked chromosome 2 markers. DNA from the tumors (but not normal tissues) in most familial cases revealed a consistent and distinct abnormality: rearrangements in short repeated sequences throughout their genomes. This abnormality suggests that a large number of replication errors had occurred during tumor development. Methods are presented for detecting the presence of the gene which predisposes people to have colon and other tumors and for utilizing this information for diagnostic, prognostic, and preventive purposes. DNA markers useful for such methods are also described.

26 Claims, 4 Drawing Sheets

TUMOR CLASSIFICATION AS INDICATION OF HEREDITARY NON-POLYPOSIS COLORECTAL CARCINOMA

This application is a division of application Ser. No. 08/452,536, filed May 30, 1995, which is a division of Ser. No. 08/056,546, filed May 5, 1993, U.S. Pat. No. 5,492,808.

This invention was made using U.S. government grants from the NIH 47527 and 35494. Therefore, the U.S. government retains certain rights to the invention.

TECHNICAL FIELD OF THE INVENTION

The invention relates to diagnostic tests for the detection of certain genes predisposing individuals to colorectal cancer. In addition, it also relates to biochemical tests which can be used to characterize tumors of the inherited form of cancer.

BACKGROUND OF THE INVENTION

The relationship of hereditary factors to the generation of common human cancers is of great scientific and public importance. In colorectal cancers, in particular, the debate about heredity and environment has gone on for almost a century. It is ironic that one of the earliest descriptions of an "inherited cancer" involved hereditary adenocarcinoma of the colon in a large family (A. S. Warthin, *Arch. Intern. Med.* 12, 546 (1913)). Yet eighty years later, there is still no proof that hereditary factors are primarily involved in such families. Part of the problem in establishing such proof is that colon cancer, like certain psychiatric disorders, are so common in, the general population that it is difficult to rule out chance clustering and other non-hereditary factors in such families. Moreover, the environment, notably diet, has been shown to play a significant role in colorectal cancer risk (B. Armstrong and R. Doll, *Int. J. Cancer* 15, 617 (1975); W. C. Willett and B. MacMahon, *N. Engl. J. Med.* 310, 697 (1984); Willett W., *Nature* 338, 389 (1989)). Members of an individual family are likely to share similar diets, further complicating definitive analysis.

We have attempted to gain evidence for a genetic component through linkage analysis. There are two major forms of colorectal cancer (CRC) predisposition that are currently recognized. The first, called familial adenomatous polyposis (FAP), is recognizable because affected patients have several unusual phenotypic features, particularly the presence of thousands of benign tumors lining the entire large intestine. FAP accounts for approximately 1% of colorectal cancer cases in the Western world (J. J. Mulvihill, in Prevention of Hereditary Large Bowel Cancer, J. R. Ingall and A. J. Mastromarino, Eds. Alan R. Liss, New York, 1983, pp. 61–75; H. J. Jarvinen, *Gut* 33, 357 (1992)) and the APC gene responsible for FAP has recently been identified (K. W. Kinzler et al., *Science* 253, 661 (1991); I. Nishisho et al., *ibid*, 665; J. Groden et al., *Cell* 66, 589 (1991); G. Joslyn et al., *ibid* 601). A second form of colorectal cancer which appears in familial patterns is called Hereditary Non-Polyposis Colorectal Cancer (HNPCC). It is more common than FAP, accounting for 5–13% of colorectal cancers in industrial nations (H. T. Lynch et al., *Cancer* 56, 939 (1985); J.-P. Mecklin, *Gastroenterology* 93, 1021 (1987); F. Kee and B. J. Collins, *Gut* 32, 509 (1991); J. R. Jass and S. M. Stewart, *Gut* 33, 783 (1992); R. S Houlston, A. Collins, J. Slack, N. E. Morton, *Ann. Hum. Genet.* 56, 99 (1992)). It is impossible to reliably distinguish individual patients with this form of CRC from "sporadic" cases on physical examination, as neither have diffuse polyposis or other unusual stigmata. A commonly used criterion for defining kindreds with HNPCC is that at least three relatives in two generations have colorectal cancer, one of the relatives diagnosed at less than 50 years of age (H. F. A. Vasen, J.-P. Mecklin, P. Meera Khan, H. T. Lynch, *Dis. Colon Rectum* 34, 424 (1991). In addition to the colon, other organs can be affected with cancer in HNPCC patients, including the endometrium, stomach, ovary, kidney; biliopancreatic system, and urinary tract (H. T. Lynch et al., *Cancer Genet. Cytogenet.* 53, 143 (1991); J. P. Mecklin and H. J. Jarvinen, *Cancer* 68, 1109 (1991)). Any individual with a family history of these cancers can be considered at risk for familial colon cancer, whether or not it conforms to the definition of HNPCC. Thus there is a need in the art for methods which will reliably distinguish hereditary (familial) from sporadic cases of colorectal cancer.

SUMMARY OF THE INVENTION

It is an object of the invention to provide methods for the detection of a gene for familial colon cancer.

It is another object of the invention to provide a nucleic acid fragment for detecting polymorphisms linked to FCC.

It is another object of the invention to provide a pair of nucleic acid primers for detecting polymorphisms linked to FCC.

It is still another object of the invention to provide methods for classifying a tumor for purposes of diagnosis and prognosis.

It is yet another object of the invention to provide kits for detecting polymorphisms linked to FCC.

These and other objects of the invention are provided by one or more of the embodiments described below. According to one embodiment of the invention a method is provided for detecting the presence in an individual of a gene for familial colon cancer (FCC). The method involves analyzing human chromosome 2 of the individual for a DNA polymorphism linked to FCC.

According to another embodiment of the invention an isolated nucleic acid fragment is provided which is useful for detecting polymorphisms linked to FCC. The fragment specifically hybridizes to human chromosome 2 at the region 2p13–21. The nucleic acid fragment is not defined by markers D2S5, D2S6, CR1L1247-M/D2S34,, D2S119, D2S123, D2S134, DS2136, D2S147, or D2S166.

According to still another embodiment of the invention a pair of nucleic acid primers for amplifying polymorphic markers linked to FCC is provided. The primers specifically hybridize to human chromosome 2 at the region 2p14–16. The primers do not amplify a marker selected from the group consisting of: D2S5, D2S6, CR1-L1247-M/D2S34, D2S119, D2S123, D2S134, DS2136, D2S147, or D2S166.

According to still another embodiment of the invention a method is provided for classifying a tumor for diagnostic and prognostic purposes comprising: determining whether at least two microsatellite markers are rearranged in a tumor of a human as compared to normal tissue of the human.

According to another embodiment of the invention a method for classifying a tumor for diagnostic and prognostic purposes is provided. The method comprises:
 determining whether at least two simple repeated sequences are rearranged in tumor tissue of a human as compared to normal tissue of the human;
 testing the human or family members of the human for the presence of the gene for familial colon cancer.

According to yet another embodiment of the invention a method for classifying a tumor for diagnostic and prognostic purposes is provided. The method comprises:

determining whether at least two simple repeated sequences are rearranged in tumor tissue of a human as compared to normal tissue of the human;

correlating the rearrangement of said simple repeated sequences with the probability of distant metastases, recurrence of the tumor, or early death.

In even another embodiment of the invention a kit is provided for detecting polymorphisms linked to FCC. The kit comprises:

at least two fragments which specifically hybridize to human chromosome 2at region 2p13–21;

a DNA polymerase for amplifying human chromosome 2 sequences.

These and other embodiments which will be clear from the more detailed disclosure which follows, provide the art with the means for diagnosis and prognosis of the most common genetic disease known.

Symbols:

■ □ male;
● ○ female;
◪ ⊘ all symbols with a diagonal, deceased;

Open symbols: no neoplasm detected.

Filled symbols:

■ colorectal or endometrial carcinoma;
⊕ other tumor of FCC spectrum;
▤ colorectal adenoma;
▩ diagnosis uncertain.

Figure 2:
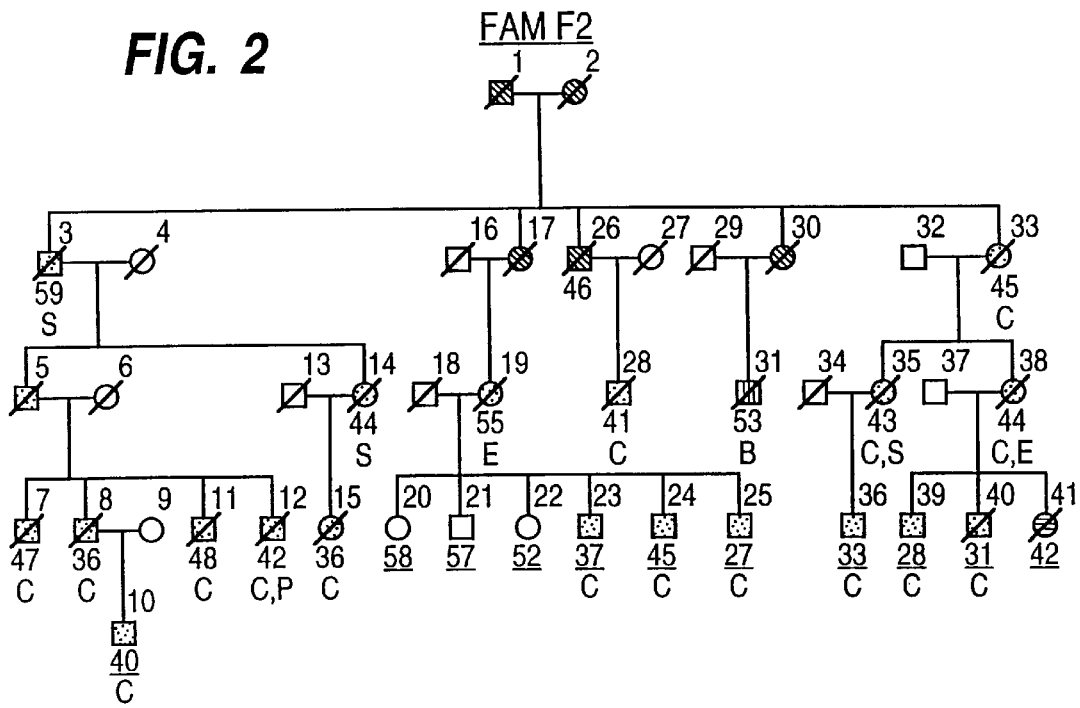
Figure 2:
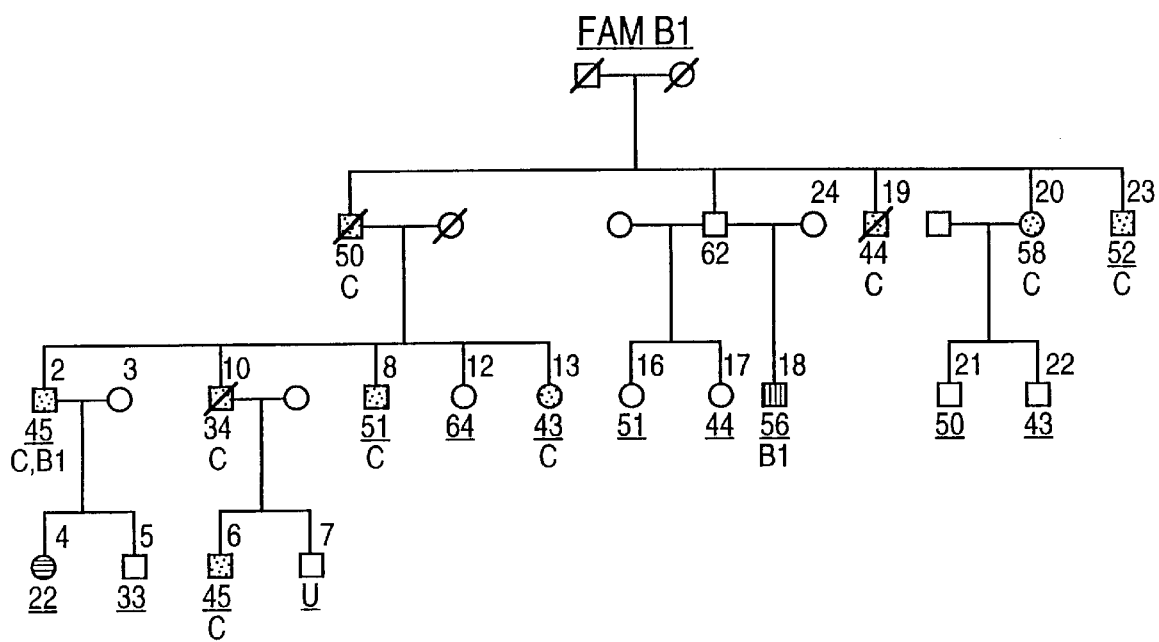

FIG. 2 shows pedigrees of families F2 and B1. Linkage data shown in Table 2 indicate that the FCC phenotype is linked to marker D2S123 (and to flanking markers, not shown) in family F2, while family B1 shows exclusion of linkage at theta=0. Numbers under the symbols indicate age at tumor diagnosis or age at last observation if unaffected. U indicates age unknown. If a blood DNA sample was available, the age is underlined. DNA samples from most of the spouses were also available, but are not indicated in the pedigrees. Letters signify the site of the tumor as above.

Symbols:

■ □ male:
● ○ female:
◪ ⊘ all symbols with a diagonal deceased
Open Symbols: No neoplasm detected.

Figure 3A:
Figure 3B:
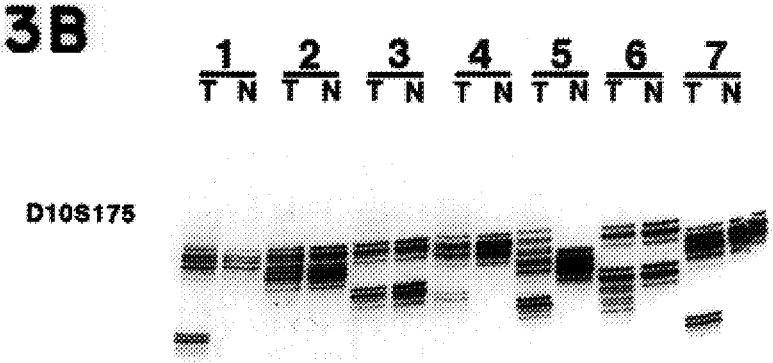

Filled Symbols:

■ colorectal or endometrial carcinoma:
⊖ colorectal adenoma:
⊕ other tumor of FCC spectrum:
▩ diagnosis uncertain:
▥ tumor not typical of FCC FIGS. 3A and 3B show dinucleotide repeat polymorphisms in normal and tumor tissue from FCC patients. The microsatellite markers D2S123 (FIG. 3A) and D10S197 (FIG. 3B) were used in PCR. Patient numbers are shown above the lanes. In each case, the lane marked "T" contains DNA from a tumor, while the lane marked "N" contains DNA from normal tissue of the same patient. Normal alleles are represented by a major band surrounded by 1–2 minor bands (J. L. Weber and P. E. May, *Am. J. Hum. Genet.* 44, 388 (1989); J. Weissenbach et al., *Nature* 359, 794 (1992)). Significant deviations were observe in tumors from patients 1, 2, 4, 5, and 7. (D2S123) and patients 1, 3, 4, 5, 6, and 7 (D10S197). All patterns shown were perfectly reproducible in replicate assays. Mixing experiments, in which tumor DNA samples were added, to normal DNA samples from other patients, demonstrated that the deviations observed in the tumors reflected intrinsic changes in the template and were not due to interference with polymerase action.

Figure 4A:
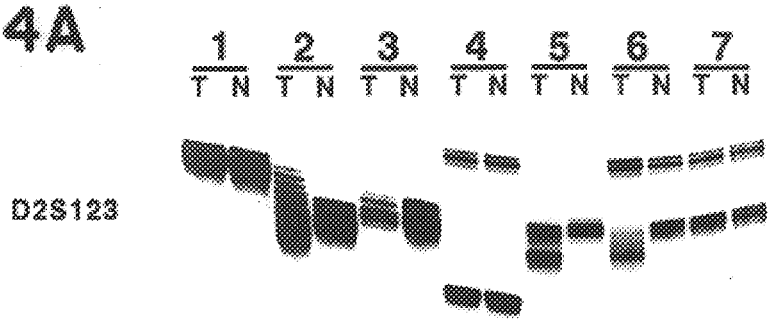
Figure 4B:
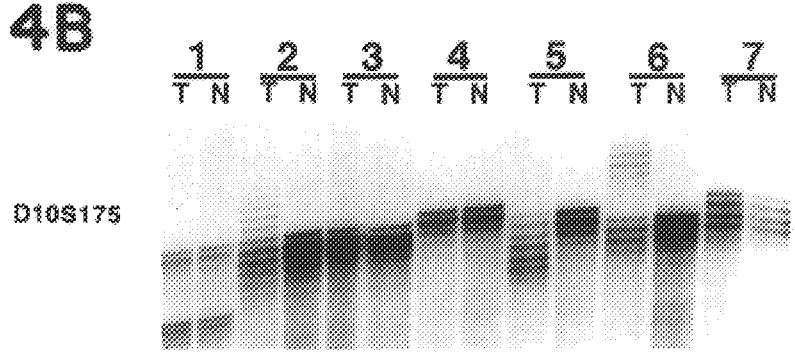

FIGS. 4A and 4B show dinucleotide repeat polymorphism in normal and tumor tissue from sporadic colorectal cancer patients. The microsatellite markers D2S123 (FIG. 4A) and D10S197 (FIG. 4B) were used in PCR and the products separated in 6% polyacrylamide gels. Patient numbers are shown above the lanes with "T" and "N" corresponding to DNA from cancerous and normal tissue, respectively. Alterations were observed in tumors 2, 5 and 6 with both markers.

DETAILED DESCRIPTION OF THE PREFERRED EMBODIMENTS

It is a discovery of the present invention that there is a single, major genetic locus responsible for familial colon cancer. The gene maps to the short arm of chromosome 2, near the anonymous marker D2S123. The gene is likely located at chromosome band 2p14–16. When mutated, the gene confers high susceptibility to colorectal cancer.

It is a further discovery of the present invention that tumors of individuals who have familial colon cancer display multiple genetic alterations. The alterations are detectable using microsatellite probes or probes to other simple repeated sequences. The multiple genetic alteration phenotype is referred to as "RER+" for replication error. RER+ tumors are classified as those in which at least two microsatellite or other simple repeated sequence markers are somatically rearranged in the tumor tissue. Patients with RER+ tumors have a significantly better prognosis than patients with RER− tumors, so this phenotype can be used by the clinician to determine treatments and predict outcomes. In addition, the strong association of RER+ phenotype to FCC makes it an indicator of the hereditary form of the disease. Thus the patient or family of a patient with an RER+ tumor may be tested for FCC to determine the susceptibility of individual family members to the disease.

According to one aspect of the invention human chromosome 2 is analyzed to determine the presence of a polymorphism which is linked to familial colon cancer (FCC). The presence of such a polymorphism indicates the presence of the gene for hereditary non-polyposis colorectal carrier. The mode of analysis can be any which is known in the art. The polymorphism can be an enzyme polymorphism or a restriction length polymorphism, or a variable number of tandem repeat polymorphism (VNTR). In order to establish the genetic linkage or connection between the desired polymorphism and the FCC gene, it is necessary to analyze a set of familial relatives of the subject under investigation. The set is chosen so that it will allow determination of whether the FCC phenotype is linked to the presence of the polymorphism. Thus, preferably, several individuals are examined. These may include an unaffected parent, an affected parent, an affected sibling, an unaffected sibling, as well as other, perhaps more distant, members. Ideally, an unaffected parent, an affected parent and an affected sibling should be utilized. If an affected parent is deceased, satisfactory results can still be obtained if unambiguous segregation of the polymorphism with the FCC gene can be demonstrated in other members.

For analysis using restriction fragment length polymorphism markers (RFLPs), blood. (or other body tissue or sample containing DNA) is obtained from all individuals being studied, including the subject. DNA is extracted from lymphocytes and digested with a particular restriction endonuclease. Optionally, several digestions can also be performed. After a digest is obtained, and separated by a standard technique, such as agarose gel electrophoresis, the separated bands (DNA fragments) can be probed with a DNA fragment which hybridizes to the RFLP. There may be a preferred combination of restriction endonuclease and probe. A general description of restriction fragment length polymorphism analysis can be found in Scientific American, Feb. 1988, vol. 258, pp. 40–48.

Preferably more than one polymorphism is used for the detection. Ideally, a polymorphism on either side of the familial colon cancer (FCC) gene will be used to increase the sensitivity. One means which can be readily employed to obtain additional polymorphic probes linked to the FCC gene is to "chromosome walk" from the D2S123 fragment. Such a method may also be expected to assist in the isolation of the actual gene for the FCC phenotype.

The particular polymorphism probe used can be of any length, so long as it is capable of identifying the polymorphism in the involved DNA region or locus. It can be a DNA fragment, or it can be present in longer genetic sequences or fragments, or even in a plasmid or other vector. Labelling and hybridization conditions can be readily determined by those of ordinary skill in the art. Usually, the hybridization stringency is standard for unique sequence DNA from within a species.

The linkage test can be carried out prenatally (on amniocytes, fetal cells in maternal blood, or chorionic villi), or presymptomatically (on blood) in young or adult individuals. It can also be performed on archival tissues, or on tissues removed for biopsy.

The method lends itself readily to the formulation of kits which can be used in diagnosis. Such a it would comprise a carrier being compartmentalized to receive in close confinement one or more containers wherein a first container may contain a DNA fragment (either probe or primers) containing sequences for a given polymorphism, i.e., an RFLP linked to FCC. A second container may contain a different set of sequences for a second RFLP linked to FCC. Other containers may contain reagents useful in the identification of the RFLP, such as DNA polymerase, deoxynucleotide triphosphates, and enzyme substrates. Still other containers may contain restriction enzymes, buffers, instructions, quality control materials, standards, and the like.

One preferred polymorphic marker according to the method of the present invention is the D2S123 marker which is linked to the D2S5 marker which has been mapped to chromosome band 2p15–16. Other probes can be obtained which map in this same region of the chromosome. These can be obtained, e.g., by chromosome walking from the D2S123 probe. Alternatively other randomly or selectively isolated fragments can be independently tested, as described herein, for linkage to familial colon cancer (FCC). Fragments can be selectively isolated, for example by cloning from FACS sorted chromosomes. Alternatively, fragments can be tested for hybridization to chromosome 2 by in situ hybridization to metaphase chromosome spreads.

Nucleic acid fragments according to the invention may be labelled as is known in the art, using enzymes, radioactive substances, or fluorescent moieties. Labeled fragments are probes which can be used to detect RFLPs or other polymorphisms, such as microsattelite or simple repeated sequences (simple sequence tandem repeats). Any labelling means as is known in the art may be used in the practice of the invention.

Polymorphisms can be detected by use of techniques other than Southern blotting. PCR amplification can be employed, for example to amplify regions containing a polymorphism. Products can be observed directly, for example by ethidium bromide staining on agarose or polyacrylamide gels, or by autoradiography if the amplified products have been radiolabeled, or by hybridization to labeled probes.

Similarly, rearrangements of microsatellite markers and other simple repeated sequences can be detected by Southern blotting, PCR amplification, or any other technique known in the art for observing particular segments of DNA. Rearrangements typically involve an increase or decrease in the copy number of the repeated sequence. Microsatellites are typically di- or tri-nucleotide repeats. Other simple repeated sequences include runs of mononucleotides.

Individuals who are found to be at risk of developing tumors, according to the present invention, may wish to modify their diet and reduce their exposure to known carcinogens, such as sunlight, tobacco smoke, aflatoxin, and the like. They also should be frequently screened to detect tumors at curable stages.

EXAMPLES

Example 1

This example demonstrates that an anonymous microsatellite marker on chromosome 2 is closely linked to the early-onset hereditary cancer phenotype.

Figure 1:
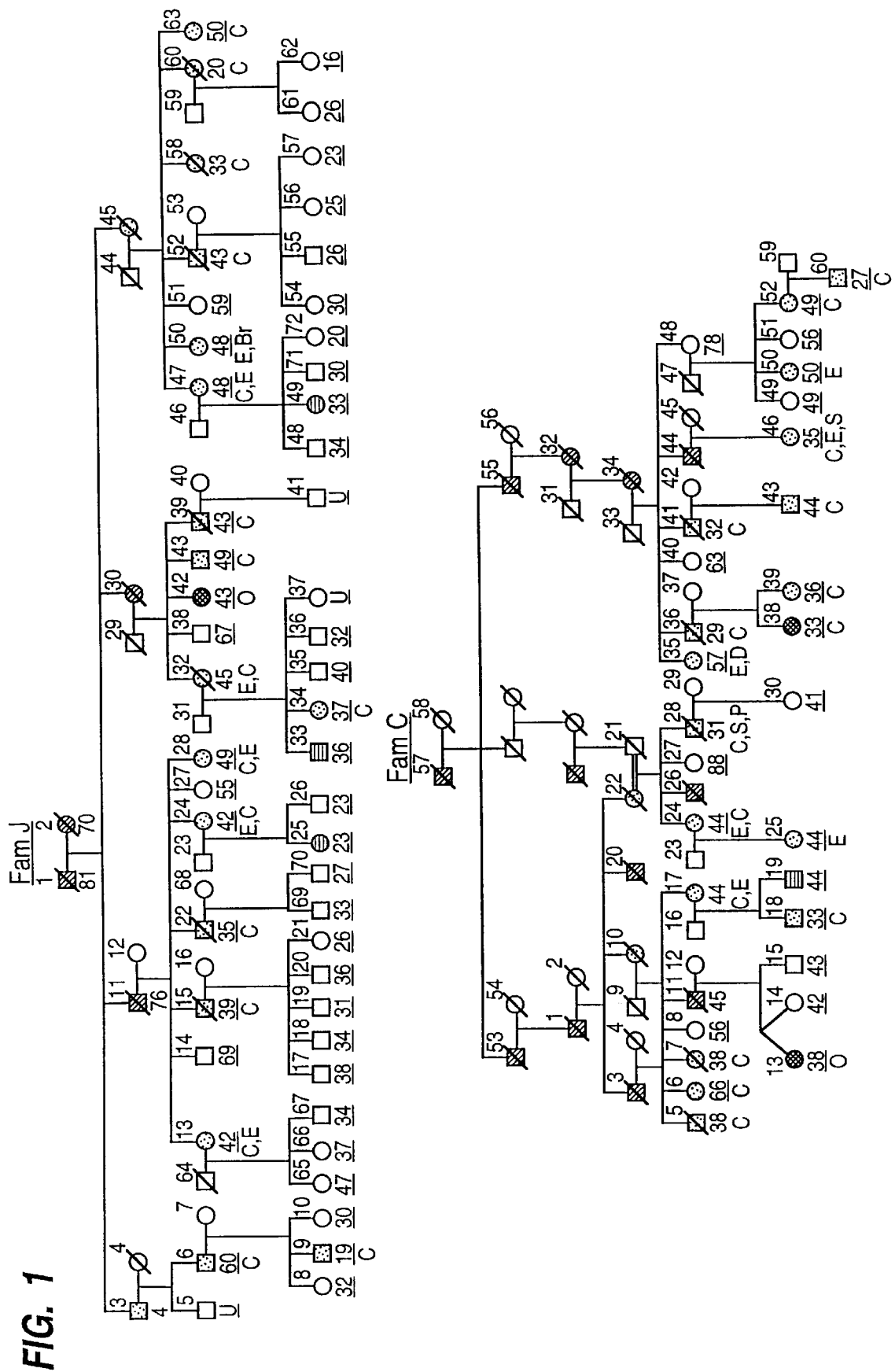
FIG. 1 provides the pedigrees of the C and J families. The status of individual family members are shown for the FCC phenotype which is defined as an individual who has at least three relatives in two generations who have colorectal cancer, one of the relatives diagnosed at less than 50 years of age. Numbers under the symbols indicate age at tumor diagnosis or age at last observation if unaffected. U indicates age unknown. If a blood DNA sample was available, the age is underlined. DNA samples from most of the spouses were also available, but are not indicated in the pedigrees. Letters signify the site of the tumor: C, colon or rectum; E, endometrium; S, stomach; D, duodenum; O, ovary; P, pancreas; BR breast. Alleles were omitted to protect the privacy of family members.

In order to prove the existence of a putative familial colon cancer gene, we studied two large pedigrees that met the FCC criteria described above. Because we were uncertain whether a single gene (rather than a compendium of genes) might be responsible for CRC in any individual family, or whether the same gene(s) would be involved in different families, we hypothesized that families sufficiently large for individual linkage analysis might prove critical in gaining statistically significant results. We thus chose two large pedigrees with FCC, families C and J, for detailed analysis. Pedigrees of the two kindreds studied are shown in FIG. 1. The C kindred originated from North America and the J kindred from New Zealand. The mean age of onset of colorectal cancer was 41.1 years (SD=13.1) and 44.4 years (SD=15.5), respectively. Extracolonic cancers were observed in both families.

Two candidate gene regions on chromosomes 18 and 5 had already been excluded as important for FCC in our previous studies (P. Peltomaki et al., *Cancer Res.* 51, 4135 (1991); P. Peltomaki et al., *Cancer Res.* 52, 4530 (1992). We therefore began a systematic search through the whole genome, using the highly informative microsatellite markers developed by Drs. Weber, Weissenbach, and colleagues (J. L. Weber and P. E. May, *Am. J. Hum. Genet.* 44, 388 (1989); J. Weissenbach et al., *Nature* 359, 794 (1992). For most microsatellite markers, PCR was done in the following final reaction conditions: 1×PCR buffer (10 mM Tris, pH 8.3; 1.5mM MgCl2; 50 mM KCl; 0.01% bovine serum albumin); 200 $\mu$M each dGTP, dATP, dTTP, 2 $\mu$M dCTP; 0.7 $\mu$Ci alpha $^{32}$I-dCTP, 3000 Ci/mmole; 10 ng each primer (1–5 primer pairs at a time); 30 ng genomic DNA template; 0.3 units AmpliTaq Polymerase (Perkin Elmer Cetus) in a volume of 10 $\mu$l. Twenty-seven cycles were performed at 94° C. for 30 sec, 55° C. for 75 sec, and 72° C. for 15 sec, and the samples were incubated at 72° C. for 6 min. following the last cycle. Electrophoresis was done using 6% polyacrylamide gels containing 7.7M urea. After electrophoresis, the gels were fixed in 10% acetic acid for 15 min, dried, and exposed to X-ray film. Altogether, 345 microsatellite markers were analyzed before convincing evidence of linkage was obtained. Marker D2S123 (AFM093xh3 J. Weissenbach et al., *Nature* 359, 794 (1992)), showed a highly significant two-point LOD score value, 6.39, at the recombination fraction (theta) of 0.0 in family C (Table 1; lower stringency criteria). The maximum pairwise LOD score for the J family was 1.45 at theta=0.0. There was no recombination between FCC and D2S123 in either family, suggesting very close linkage. With two flanking markers, D2S119 (distal to D2S123 ) and D2S136 (proximal to D2S123 ), recombination was observed in both families, and the maximum pairwise LOD scores shown by D2S119 and D2S136, respectively, were 0.50 at theta$_{max}$=0.16 and 0.58 at theta$_{max}$=0.18 for family C and 3.49 at theta$_{max}$=0.08 and 1.66 at theta$_{max}$=0.11 for family J (Table 1; lower stringency criteria).

In linkage calculations, individuals with different neoplasms were treated as follows. Colorectal and endometrial carcinoma (the two most common cancers in FCC family members; H. T. Lynch et al., *Cancer Genet. Cytogenet.* 53, 143 (1991); J. P. Mecklin and H. J. Jarvinen, *Cancer* 68, 1109 (1991); T. Hakala, J-P. Mecklin, M. Forss, H. Jarvinen, P. Lehtovirta, *Cancer* 68, 1656 (1991)) were considered as definitive manifestations of the disorder. Individuals with a colorectal adenoma or with a single carcinoma of the ovary, stomach, hepatobiliary system, small intestine, kidney, or ureter were classified as either having an unknown status (high stringency analysis) or as being affected (low stringency analysis). Multipoint linkage analysis was carried out separately in families C and J by program LINKMAP of the LINKAGE program package with the no sex difference option (G. M. Lathrop, J. M. Laloueol C. Julier, J. Ott, *Proc. Natl. Acad. Sci. USA* 81, 3443 (1984)). A fixed map of the markers used was computed from the available data in the CEPH version 6.0 database. Flanking marker distances to D2S123 were 11 cM and 14 cM for D2S119 and D2S136, respectively. The FCC gene maps with D2S123 giving a four-point LOD score of 6.47 in family C and 6.01 in family J at 0 recombination.

The physical location of marker D2S123 has not yet been directly determined. The approximate locations for the markers used in multipoint linkage analyses were obtained from a genome mapping effort including a total of 96 markers from chromosome 2 . The calculations placed locus D2S123 5 cM distal to D2S5 which has been mapped to 2p15–16 by in situ hybridization, linkage, and somatic cell hybrid analysis (Y. Shiloh et al., *Nucl. Acids Res.* 13, 5403 (1985); H. Donis-Keller et al., *Cell* 51, 319 (1987); A. J. Pakstis, C. M. Castiglione, J. R. Kidd, *Cytogenet. Cell Genet.* 51, 1057 (1989)). Thus, the most likely physical location of the FCC gene is 2p15–16.

The established linkage is unequivocal. Changes in different parameters did not have any major effect on the results. We varied the following parameters: (1) affection status (more vs. less stringent criteria as detailed above) and (2) FCC gene frequency (0.001 vs. 0.01 or 0.0005). In the J family, low stringency criteria resulted in an increase in the LOD score values for D2S123 and a decrease in those for D2S136 while in family C the stringency of criteria did not have any essential effect on the results (Table 1). Variation of the FCC gene frequency had practically no influence on the LOD score values (for example, using the frequency of 0.01 the maximum LOD scores for D2S123 were 6.18 in family C and 1.38 in family J, both at 0 recombination).

The localization of an FCC gene to chromosome 2 in kindreds from two different continents essentially proves that this is a genetically determined disease. Many precedents suggest that any gene which plays a role in a hereditary form of cancer is likely to be involved in a significant number of "sporadic" cases of the same tumor type, by virtue of somatic mutations, germline alterations or inherited alterations that are poorly penetrant (E. J. Stanbridge, *Ann. Rev. Genet.* 24, 615 (1990); R. A. Weinberg, *Science* 254, 1138 (1991); A. G. Knudson, *Cancer Res.* 45, 1437 (1985); E. R. Fearon and B. Vogelstein, *Cell* 61, 759 (1990)). The current study lays the groundwork for mapping, isolation, and characterization of the FCC gene on chromosome 2 , and the examination of its role in colorectal and other tumors. If, as expected, this gene is involved in a significant fraction of familial colorectal cancer cases, it is responsible for the most common form of heritable disease yet identified in humans (H. T. Lynch et al., *Cancer* 56, 939 (1985); J.-P. Mecklin, *Gastroenterology* 93, 1021 (1987); F. Kee and B. J. Collins, *Gut* 32, 509 (1991); J. R. Jass and S. M. Stewart, *Gut* 33, 783 (1992); R. S. Houlston, A. Collins, J. Slack, N. E. Morton, *Ann. Hum. Genet.* 56, 99 (1992). The study of such a gene has obvious implications for public health. Most immediately, these results make presymptomatic diagnosis of susceptibility possible in FCC family members and will thus enable more effective surveillance programs for early detection and treatment of cancer.

TABLE 1

Pairwise analysis of linkage vs. FCC by the MLINK program of the LINKAGE program package (G. M. Lathrop, J. M. Lalouel, C. Julier, J. Ott, Proc. Natl. Acad. Sci USA 81, 3443 (1984)). Sex averaged LOD scores are shown separately for families C and J under two different phenotypic criteria. Individuals with adenoma or a single carcinoma other than that of colon or endometrium were considered either to be affected (lower stringency) or to have an unknown status (higher stringency) Phenotypes were as affected with an autosomal dominant made of inheritance and four liability classes according to the age at the time of observation (healthy) or at the time of diagnosis. Penetrances for heterozygotes were set at 0.15 at age 30 years or below (liability class 1), 0.40 at age 31–45 years (liability class 2), 0.70 at age 46–60 years (liability class 3), and 0.90 at age 61 or over (liability class 4). Phenocopies were allowed, with frequencies set at 1%, 3%, and 5% in liability classes 2, 3, and 4, respectively. The frequency of the FCC gene was set as 0.001 (but values of 0.01 and 0.0005 were also tested, see text). The allele frequencies of markers D2S119, D2S123, and D2S136 were calculated from 53–58 spouses of FCC family members.

| Marker | Family | Criteria stringency | 0 | 0.001 | 0.01 | 0.05 | 0.1 | 0.2 | 0.3 | 0.4 | $Z_{max}$ | $\theta_{max}$ |
|---|---|---|---|---|---|---|---|---|---|---|---|---|
| D2S119 | C | lower | -1.08 | -1.02 | -0.63 | 0.11 | 0.42 | 0.48 | 0.30 | 0.11 | 0.50 | 0.16 |
|  |  | higher | -0.37 | -0.32 | -0.04 | 0.47 | 0.63 | 0.55 | 0.32 | 0.12 | 0.64 | 0.12 |
|  | J | lower | 1.81 | 2.07 | 2.81 | 3.43 | 3.47 | 2.96 | 2.10 | 1.00 | 3.49 | 0.08 |
|  |  | higher | 2.21 | 2.45 | 3.07 | 3.43 | 3.32 | 2.71 | 1.86 | 0.86 | 3.43 | 0.05 |
| D2S123 | C | lower | 6.39 | 6.38 | 6.28 | 5.82 | 5.21 | 3.91 | 2.49 | 1.04 | 6.39 | 0.00 |
|  |  | higher | 5.24 | 5.23 | 5.14 | 4.75 | 4.25 | 3.15 | 1.97 | 0.79 | 5.24 | 0.00 |
|  | J | lower | 1.45 | 1.44 | 1.42 | 1.30 | 1.15 | 0.83 | 0.53 | 0.24 | 1.45 | 0.00 |
|  |  | higher | 0.85 | 0.85 | 0.83 | 0.75 | 0.66 | 0.47 | 0.30 | 0.14 | 0.83 | 0.00 |
| D2S136 | C | lower | -1.47 | -1.42 | -1.02 | -0.06 | 0.39 | 0.57 | 0.39 | 0.13 | 0.58 | 0.18 |
|  |  |  | -1.03 | -0.99 | -0.64 | 0.13 | 0.45 | 0.50 | 0.30 | 0.09 | 0.53 | 0.16 |
|  | J | lower | 1.15 | 1.15 | 1.22 | 1.53 | 1.66 | 1.47 | 1.00 | 0.40 | 1.66 | 0.11 |
|  |  | higher | 2.38 | 2.39 | 2.43 | 2.46 | 2.33 | 1.84 | 1.18 | 0.46 | 2.47 | 0.04 |

Example 2

This example demonstrates that several additional families are likely to be linked to the FCC locus on chromosome 2, while other families are likely to be unlinked.

Stimulated by the finding that chromosome 2 markers were closely linked to cancer predisposition in two large kindreds with FCC (see Example 1), we went on to study 14 smaller kindreds. Pedigrees of two of these families are shown in FIG. 2. As predicted by simulated analysis, linkage information to conclusively prove or rule out linkage to these markers could only be obtained assuming particularly favorable allele distributions. Results of linkage analyses using marker D2S123 that is closely linked to FCC are shown in Table 2. In these calculations, individuals with colorectal cancers, with other FCC associated cancers (H. F. A. Vasen, J-P. Mecklin, P. Meera Khan, H. T. Lynch, Dis. Colon Rectum 34, 424 (1991)), or with colorectal adenomas were classified as "affected", as outlined above. The results reflect the limited amount of linkage information that can be derived from these families in spite of the highly informative nature of the D2S123 marker (heterozygosity 0.78 calculated from 58 unrelated spouses in these 16 families). The difficulty derives from the fact that affected members of these pedigrees are often dead from their disease (so unavailable for analysis), while most living members without evident cancer are too young to reliably classify as unaffected. Despite these problems, formal exclusion of linkage (LOD score<2.0) was obtained in families F11, B1 and B2 while the remaining 11 smaller families displayed varying degrees of positive and negative results. The HOMOG program was used to calculate conditional probabilities ($P_{cond}$) of linkage as shown in Table 1, and this test revealed clear-cut heterogeneity (p<0.0005 by Chi$^2$). This suggested that several families with positive LOD scores are likely to be linked, while an equal number of others might be unlinked to the FCC locus on chromosome 2.

TABLE 2

Heterogencity test results (A-test as implemented in program HOMOG, courtesy of Prof. J. Ott) for 16 families tested for anonymous DNA marker D2S123. LOD score values (Z) for each family at zero recombination fraction (θ, the conditional probability of belonging to a linked type ($P_{cond}$), and the estimates approximate confidence limits are given where appropriate. The test is based on results of pairwise linkage analyses using the low stringency criteria described in the text with an FCC gene frequency set at 0.001. The p-value derived from the maximum likelihood estimate of the proportion of linked family types (α) and theta for the heterogencity of the linkage data is given in the footnote. The approximate 95% confidence limits for α and θ were 0.05–0.73 and 0.000–0.10, respectively.

| FAMILY | # OF AFFECTED INDIVIDUALS IN KINDRED | # OF AFFECTED INDIVIDUALS ANALYZED | MEDIAN AGE AT DIAGNOSIS (YEARS) | D2S123, Z AT θ = 0 | $P_{cond}$ | 95% CONFIDENCE LIMITS |
|---|---|---|---|---|---|---|
| C* | 22 | 13 | 39.7 | 6.39 | 1 | — |
| J* | 23 | 85 | 40.5 | 1.45 | 0.9356 | 0.5918–0.9870 |
| F3 | 21 | 7 | 41.2 | 0.59 | 0.6671 | 0.1667–0.9132 |
| F3 | 9 | 5 | 47.3 | 0.83 | 0.7769 | 0.2580–0.9481 |

TABLE 2-continued

Heterogencity test results (A-test as implemented in program HOMOG, courtesy of Prof. J. Ott) for 16 families tested for anonymous DNA marker D2S123. LOD score values (Z) for each family at zero recombination fraction (θ, the conditional probability of belonging to a linked type ($P_{cond}$), and the estimates approximate confidence limits are given where appropriate. The test is based on results of pairwise linkage analyses using the low stringency criteria described in the text with an FCC gene frequency set at 0.001. The p-value derived from the maximum likelihood estimate of the proportion of linked family types (α) and theta for the heterogencity of the linkage data is given in the footnote. The approximate 95% confidence limits for α and θ were 0.05–0.73 and 0.000–0.10, respectively.

| FAMILY | # OF AFFECTED INDIVIDUALS IN KINDRED | # OF AFFECTED INDIVIDUALS ANALYZED | MEDIAN AGE AT DIAGNOSIS (YEARS) | D2S123, Z AT θ = 0 | $P_{cond}$ | 95% CONFIDENCE LIMITS |
|---|---|---|---|---|---|---|
| F6 | 7 | 4 | 44.9 | −0.16 | 0.2628 | 0.0351–0.6823 |
| F8 | 8 | 3 | 42.4 | −0.95 | 0.0546 | 0.0059–0.4666 |
| F10 | 9 | 5 | 46.0 | −1.52 | 0.0153 | 0.0016–0.3452 |
| F11 | 7 | 6 | 44.5 | −2.28 | 0.0027 | 0.0003–0.2876 |
| 539 | 4 | 3 | 41.8 | −1.10 | 0.0393 | 0.0042–0.4839 |
| F56 | 6 | 5 | 49.0 | 0.00 | — | — |
| F59 | 6 | 5 | 54.8 | 0.44 | 0.5866 | 0.1266–0.8816 |
| B1 | 11 | 6 | 47.2 | −2.17 | 0.0035 | 0.0004–0.1957 |
| B2 | 12 | 4 | 56.5 | −2.33 | 0.0024 | 0.0002–0.2223 |
| B3 | 8 | 4 | 40.7 | 0.08 | 0.3825 | 0.0595–0.7647 |
| B4 | 10 | 5 | 55.6 | 0.12 | 0.4044 | 0.0649–0.8245 |
| B5 | 8 | 7 | 51.0 | −1.80 | 0.0081 | 0.0008–0.1957 |

$X^2$het = 11.013, p = 0.0005 at θ = 0, α = 0.34
*Studied in (Example 1).

Example 3

This example demonstrates that genes implicated in sporadic colorectal cancer are also involved in FCC.

We next examined oncogenes and tumor suppressor genes that have been demonstrated to undergo somatic mutations in sporadic colorectal cancers. We reasoned that, if the pathogenesis of familial CRC differed from that of the more common sporadic forms, then genes previously implicated in the latter may not be involved. For this investigation, we studied 18 tumors derived from 18 patients from 15 different FCC kindreds. One of these kindreds could be shown by linkage analysis to be probably linked to chromosome 2, one was probably unlinked, and the others were derived from families uninformative or not studied for linkage.

We first looked at the K-RAS gene, mutations of which occur relatively early in sporadic colorectal tumors but do not generally initiate the tumorigenic process. K-RAS mutations at codons 12 or 13 were identified in 58% of the eighteen tumors studied, a percentage slightly higher than that found in sporadic cases (approximately 40%, J. Bos et al., Nature 327, 293 (1987); K. Forrester et al., Nature 327, 298 (1987); B. Vogelstein et al., N. Engl. J. Med. 319, 525 (1988); The K-ras gene was amplified via the polymerase chain reaction, as described in D. Sidransky et al., Science 256, 102 (1992). Mutations in codons 12 and 13 were analyzed using a modified ligation assay [U. Landegren et al., Science 241, 1077 (1988)]. Eleven mutations were observed in the 18 tumors analyzed, consisting of 3 glycine to valine and 5 glycine to aspartic acid substitutions at codon 12, and 3 glycine to aspartic acid substitutions at codon 13; E. R. Fearon and B. Vogelstein, Cell 61, 759 (1990); Table 3).

Similarly, p53 gene alterations, which generally occur late in tumorigenesis (often at the transition between benign and malignant states, E. R. Fearon and B. Vogelstein, Cell 61, 759 (1990)), were found in approximately thee same proportion of familial and sporadic cancers (64% and 61%, respectively), p53 mutations were evaluated by immunohistochemistry of cryostat sections, using monoclonal antibody 1801 (Oncogene Science), as described previously for sporadic cancers [N. R. Rodriguez et al., Proc. Natl. Acad. Sci. U.S.A. 87, 7555 (1990); F. M. van den Berg et al., J. Pathology 157, 193 (1989); E. Campo et al., Cancer Res. 51, 4436 (1991)]. A clonal pattern of nuclear staining indicative of mutation was observed in 64% of the 11 familial colorectal cancer cases analyzed, similar to the 61% previously observed in sporadic colorectal cancers (Table 3).

We finally evaluated the APC gene. Mutations in APC are thought to initiate most sporadic colorectal tumors (S. M. Powell et al., Nature 359, 235 (1992)), and germline mutations of APC are found in Familial Adenomatous Polyposis (FAP), a syndrome which predisposes to CRC (K. W. Kinzler et al., Science 253, 661 (1991); I. Nishisho et al., ibid 253, 665 (1991); J. Groden et al., Cell 66, 589 (1991); G. Joslyn et al., Cell 66, 601 (1991)). FAP is distinguished from HNPCC by its association with the development of numerous benign colorectal polyps in addition to CRC. In contrast, HNPCC or FCC is generally associated with no phenotypic manifestations other than a high incidence of cancer. One intriguing possibility was that mutations in an HNPCC or FCC gene could substitute for APC in the tumorigenic process, and that tumors would progress along either an "APC" or "FCC" pathway. This possibility was ruled out by finding that 57% of the familial cancers had mutations in APC when screened by methods that revealed mutations in 49% of sporadic cancers. (Mutations producing translation termination between APC codons 686-2256 were evaluated using a PCR-based strategy. DNA encoding codons 686-2256 was amplified in three overlapping fragments, and the fragments were evaluated for stop codons as described. Mutations detected by this assay were found in 49% of sporadic colorectal tumors previously evaluated (Powell et al., S. M. Powell et al., Nature 359, 235 (1992)), Table 3).

TABLE 3

Somatic mutations of oncogenes and tumor suppressor genes in cancers from FCC and sporadic cases.
NUMBER OF TUMORS MUTATED

|  | KRAS | p53 | APC |
|---|---|---|---|
| FCC: | 11/18 (61%) | 7/11 (64%) | 8/14 (57%) |
| SPORADIC: | 37/92 (40%) | 81/132 (61%) | 20/41 (49%) |
| REPERENCES: | J. Bos et al., Nature 327, 293 (1987); K. Forrester et al., Nature 327, 298 (1987); B. Vogelstein et al., N. Engl. J. Med. 319, 525 (1988); The K-ras gene was amplified via the polymerase chain reaction, as described in D. Sidransky et al., Science 256, 102 (1992). Mutations in codons 12 and 13 were analyzed using a modified ligation assay [U. Landegren et al., Science 241, 1077 (1988)]. Eleven mutations were observed in the 18 tumors anaiyzed; consisting of 3 glycine to valine and 5 glycine to aspartic acid substitutions at codon 12, and 3 glycine to aspartic acid substitutions at codon 13 | p53 mutations were evaluated by immunohistochemistry of cryostat sections, using monoclonal antibody 1801 (Oncogene Science), as described previously for sporadic cancers [N.R. Rodriguez et al., Proc. Natl. Acad. Sci. U.S.A. 87, 7555 (1990); F. M. van den Berg et al., J. Pathology 157, 193 (1989); E. Campo et al., Cancer Res. 51, 4436 (1991)]. A clonal pattern of nuclear staining indicative of mutation was observed in 64% of the 11 familial colorectal cancer cases analyzed, similar to the 61% previously observed in sporadic colorectal cancers | Mutatioris pmducing transiation termination between APC codons 686–2256 were evaluated using a PCR-based strategy. DNA encoding codons 686–2256 was amplified in three overlapping fragments, and the fragments were evaluated for stop codons as described (S. M. Powell et al submitted). Mutations detected by this assay were found in 49% of sporadic colorectal tumors previously evaluated (Powell et al., S. M. Powell et al., Nature 359, 235 (1992)) |

Example 4

This example demonstrates that the majority of FCC tumors display an altered electrophoretic mobility of dinucleotide and trinucleotide repeat fragments. This phenotype is called RER+ for "replication errors".

Because other genes responsible for cancer predisposition undergo losses in tumors (E. J. Stanbridge, *Ann. Rev. Genet.* 24, 615 (1990); R. A. Weinberg, *Science* 254, 1138 (1991); A. G. Knudson, *Cancer Res.* 45, 1437 (1985); E. R. Fearon and B. Vogelstein, *Cell* 61, 759 (1990)), we searched for loss of heterozygosity at the D2S123 locus by studying DNA extracted from tumor tissues and comparing it with matched normal DNA from the same individuals. DNA was prepared from cryostat sections of tumors after removal of contaminating areas of normal tissue, as described in Vogelstein N. Engl. J. Med. 319, 525 (1988) and the products separated in 6% polyacrylamide gels. Contrary to expectation, this locus was found to be deleted in none of the 14 FCC tumors and in only one of the, 46 sporadic tumors examined. However, a remarkable and unexpected pattern of changes was observed in the majority of the FCC derived tumors in this analysis. These changes consisted of shifts in the electrophoretic mobility of $(CA)_n$ dinucleotide repeat fragments, suggesting that replication errors (RER) had occurred in these sequences during tumor development (FIG. 3). Similar shifts were seen much more rarely in sporadic CRC tumors (see below). To investigate whether the shifts were confined to marker D2S123, we searched for shifts using $(CA)_n$ markers D2S119 and D2S147, located approximately 10 cM on either side of D2S123, as well as markers D11S904, D13S175 and D10S197, representing other chromosomes. All of these markers showed significant alterations in tumor DNA, with 43%–71% of the tumors showing shifts with each probe used (examples in FIG. 3; Table 4). To determine whether such alterations were confined to $(CA)_n$ dinucleotide repeats, we also studied CTG-B37, a $(CAG)_n$ trinucleotide repeat from the coding region of a recently identified gene on chromosome 12 (S-H. Li et al., *Genomics*, in press). As indicated in Table 4, shifts were also observed frequently with this probe. The alterations shown in FIG. 3 and summarized in Table 4 were distributed non-randomly among the tumors analyzed. Eleven of the fourteen tumors had shifts in at least two of the seven markers studied and were categorized as RER+. The other three tumors were designated as RER−, and had a markedly different fraction of abnormalities with every marker tested.

TABLE 4

Microsatellite alterations in FCC and sporadic tumors.
The percentage of tumors with alterations of each of the
microsatellite markers studied is listed for each tumor type.

| TUMOR* TYPE | NUMBER OF TUMORS | D2 S123 | D2 S147 | D2 S119 | D11 S904 | D13 S175 | D10 S197 | CTG B37 |
|---|---|---|---|---|---|---|---|---|
| FCC |  |  |  |  |  |  |  |  |
| RER+ | 11** | 91% | 55% | 55% | 55% | 64% | 91% | 55% |
| RER− | 3*** | 0% | 0% | 0% | 0% | 0% | 0% | 0% |
| TOTAL SPORADIC | 14 | 71% | 43% | 43% | 43% | 50% | 71% | 43% |
| RER+ | 6 | 67% | 83% | 83% | 67% | 100% | 83% | 67% |
| RER− | 40 | 0% | 0% | 0% | 0% | 0% | 2% | 0% |
| TOTAL | 46*** | 9% | 11% | 11% | 9% | 13% | 13% | 9% |

*RER+ tumors were defined as those with alterations in at least two of the indicated microsatellite markers.
**9 colorectal carcinomas, 1 colorectal adenoma, and 1 ovarian carcinoma.
***All colorectal carcinomas

Example 5

This example demonstrates the presence of the RER+ phenotype in a subset of sporadic colorectal cancers.

Forty-six sporadic colorectal cancers and corresponding normal tissues were then evaluated using the same markers. The sporadic tumors had a much lower incidence of shifts than the FCC tumors ($p<0.000001$ for all markers combined and $p<0.01$ for each of the 7 markers tested, by $Chi^2$). Moreover, the tumors could obviously be divided into two subsets. Six of the 46 tumors had shifts in at least two of the markers tested, and by analogy to the FCC tumors, were categorized as RER+. These six patients ranged in age from 62–82 years (mean 75) and none had a family history meeting FCC criteria. As with the FCC tumors, there was a dramatic difference between the RER+ and RER− tumors with every marker assessed (Table 4). As can be seen from FIGS. 3 and 4, some of the shifts in the RER+ tumors resulted in alleles larger than those present in the normal tissue, while other shifts resulted in smaller alleles.

These observations prompted us to determine whether the RER+ tumors had biologic features in common with the tumors from FCC patients. The latter tumors often occur on the right side of the colon (H. T. Lynch et al., Dis. Colon Rectum 20, 661 (1977); J-P. Mecklin and H. J. Järvinen, Dis. Colon Rectum 29, 160 (1986)) and are frequently diploid or near diploid (M. Kouri et al., Cancer 65, 1825 (1990)). The RER+ sporadic tumors displayed both these features. All six of the RER+ sporadic cancers occurred on the right side of the colon, whereas only 17 of 40 of the RER− tumors were right sided ($p<0.01$, by $Chi^2$). "Diploidy" was evaluated in a quantitative fashion using allelotype assays. In such assays, each chromosomal arm is assessed for loss using a panel of cloned probes detecting restriction fragment length polymorphisms upon Southern blotting. (All of the sporadic tumors evaluated here for RER have been previously assessed for fractional allelic loss (FAL) (B. Vogelstein et al., Science 244, 207 (1989)). Despite the frequent changes in dinucleotide and trinucleotide repeats in the RER+ tumors, VNTR repeat alleles were not similarly affected. Over thirty VNTR polymorphisms distributed throughout the genome were assessed. Additionally, no single base pair changes resulting in altered site polymorphisms were identified in the RER+ tumors when studied with more than 30 site polymorphic markers (ibid and S. J. Baker et al., Science 244, 217 (1989)). The fraction of chromosomal arms which undergo allelic loss (FAL) is therefore a molecular measure of chromosome imbalance. The FAL average $0.039\pm(SD=0.034)$ in the six RER+ tumors, six fold lower than the 0.254 (SD=0.142) value found in the forty RER− cases ($p<0.001$, by Student's t-Test).

Presently the nature of the mapped FCC gene is not known, but the studies described here provide some important clues as to how it might act. First, previously discovered tumor suppressor genes frequently are the targets of allelic loss in tumor tissues. If the remaining allele is mutant, the cell is left with no functional suppressor gene product, so tumor initiation or progression ensues. The demonstrated absence of allelic loss in FCC tumors argues against its being a typical recessively acting tumor suppressor gene (E. J. Stanbridge, Ann. Rev. Genet. 24, 615 (1990); R. A. Weinberg, Science 254, 1138 (1991); A. G. Knudson, Cancer Res. 45, 1437 (1985); E. R. Fearon and B. Vogelstein, Cell 61, 759 (1990)). In contrast, the clonal genome-wide shift in microsatellite marker allele sizes observed in the majority of FCC tumors argues in favor of a different mechanism generating susceptibility to tumor formation. Microsatellites are present every 100,000 bp in genomic DNA (J. L. Weber and P. E. May, Am. J. Hum. Genet. 44, 388 (1989); J. Weissenbach et al., Nature 359, 794 (1992)), and if the results recorded in Table 4 are extrapolated, it can be predicted that the cancer cell genome in the RER+ cases contains thousands of changes compared to the genome of normal cells from the same patients. Altered mononucleotide repeats have been independently observed in sporadic colorectal cancers (M. Perucho, oral disclosure, Madrid, Spain, April, 1992). Although many such changes may be silent, some may lead to significant alterations in gene products or expression levels. For example, trinucleotide repeats are also affected in these tumors (CTG-B37 in Table 4), and such repeats are often found in the coding regions of genes (C. T. Caskey et al., Science 256, 784 (1992)). Although the rate of change in these sequences cannot be easily measured in tumor tissues, the data are consistent with the idea that genetic instability is a component of the familial cancer phenotype. There is ample precedent for this concept in tumor biology. For example, patients with xeroderma pigmentosum, ataxia telangiectasia, and Bloom's syndrome have a genetic instability (in some cases revealed by mutagens) that results in a predisposition to cancer (P. J. McKinnen, Hum. Genet. 175, 197 (1987); J. E. Cleaver, Nature 218, 652 (1968); J. German, D. Bloom, and E. Passarge, Clin. Genet. 35, 57 (1989)). Though these latter syndromes are inherited as recessive diseases, there is no reason that a dominantly acting gene could not produce a similar result. A subtly altered replication factor, for example, would be a good candidate for the FCC gene. One might not expect allelic losses of such a gene, as such loss, coupled with mutation of the remaining allele, would be incompatible with cellular replication. This hypothesis is also consistent with the observation that cancer susceptibility in FCC kindreds is not confined to the colorectal epithelium, as affected individuals often develop other tumors (J-P. Mecklin and H. J. Jarvinen, Cancer 68, 1109 (1991); H. T. Lynch et al., Cancer Genet. Cytogenet. 53, 143 (1991)). It is notable in this regard that in the FCC ovarian cancer studied here, 6 of the 7 microsatellite markers studied were altered (Table 4).

These results have straightforward practical implications. Because CRC is so common, it is difficult to know which families have a true familial predisposition and which represent chance clustering. In fact, we could not rule out the possibility that the apparent absence of chromosome 2 linkage in some families (Table 2) was not due to the admixture of "sporadic" cases. Although only half of the FCC kindreds provided some positive evidence for linkage, ten of thirteen families whose tumors were studied had RER+ tumors, and these ten included one "unlinked" kindred (F11 in Table 1) and seven kindreds in which linkage analysis was impossible or equivocal. Moreover, the data in Table 3 show that 13% of "sporadic" CRC patients had the same RER abnormality in their tumors. This proportion is in good agreement with previous estimates of familial colon cancer incidence (R. S. Houlston, A. Collins, J. Slack, N. E. Morton, Ann. Hum. Genet. 56, 99 (1992)), and the RER+ patients had biologic features in common with cancers from patients in clearly defined FCC kindreds. Thus, RER analysis might considerably augment standard linkage studies. Relatives of patients with RER+ tumors may be at particular risk for developing cancers of the colon and other organs. Recognition of this risk, by the simple assays described here, could thereby have significant consequences for prevention.

We claim:

1. A method for classifying a tumor for diagnostic and prognostic purposes comprising:

determining whether at least two microsatellite markers are rearranged in tumor tissue of a human as compared to normal tissue of the human; and testing the human or family members of the human for the presence of the gene for familial colon cancer (FCC) by detecting the presence or absence of a DNA polymorphism on a human chromosome band 2p13–21 in nucleic acids from said human or family member, wherein the presence of said DNA polymorphism is correlated with the presence of a familial colon cancer gene.

2. A method for classifying a tumor for diagnostic and prognostic purposes comprising:

determining whether at least two simple repeated sequences are rearranged in tumor tissue of a human as compared to normal tissue of the human;

testing the human or family members of the human for the presence of the gene for familial colon cancer by detecting the presence or absence of a DNA polymorphism on a human chromosome band 2p13–21 in nucleic acids from said human or family member, wherein the presence of said DNA polymorphism is correlated with the presence of a familial colon cancer gene.

3. The method of claim 2 wherein said step of determining is performed by the steps of:

(a) digesting DNA from a tumor of an individual with a restriction endonuclease to form tumor DNA fragments;

(b) separating said tumor DNA fragments;

(c) hybridizing said tumor DNA fragments to a polymorphism-detecting probe to provide a first hybridization pattern, said polymorphism-detecting probe containing simple repeated sequences;

(d) digesting DNA from normal tissue of the individual with the restriction endonuclease to form normal DNA fragments;

(e) separating said normal DNA fragments;

(f) hybridizing said normal DNA fragments to the polymorphism-detecting probe to provide a second hybridization pattern;

(g) comparing the first and second hybridization patterns;

(h) performing each of steps (a)–(g) with at least a second polymorphism-detecting probe, said second probe containing simple repeated sequences.

4. The method of claim 2 wherein said step of determining is performed by the steps of:

(a) amplifying a first region of DNA from a tumor of an individual to form tumor DNA fragments, said first region of DNA containing simple repeated sequences;

(b) separating said tumor DNA fragments to provide a first DNA fragment pattern;

(c) amplifying the region of DNA from normal tissue of the individual to form normal DNA fragments;

(d) separating said normal DNA fragments to provide a second DNA fragment pattern;

(e) comparing the first and second DNA fragment patterns; and (f) performing each of steps (a)–(e) with at least a second region of DNA containing simple repeated sequences.

5. The method of claim 1 wherein said step of determining is performed by the steps of:

(a) digesting DNA from a tumor of an individual with a restriction endonuclease to form tumor DNA fragments;

(b) separating said tumor DNA fragments;

(c) hybridizing said tumor DNA fragments to a microsatellite probe to provide a first hybridization pattern;

(d) digesting DNA from normal tissue of the individual with the restriction endonuclease to form normal DNA fragments;

(e) separating said normal DNA fragments;

(f) hybridizing said normal DNA fragments to the microsatellite probe to provide a second hybridization pattern;

(g) comparing the first and second hybridization patterns;

(h) performing each of steps (a)–(g) with at least a second microsatellite probe.

6. The method of claim 1 wherein said step of determining is performed by the steps of:

(a) amplifying a microsatellite region of DNA from a tumor of an individual to form tumor DNA fragments;

(b) separating said tumor DNA fragments to provide a first DNA fragment pattern;

(c) amplifying the microsatellite region of DNA from normal tissue of the individual to form normal DNA fragments;

(d) separating said normal DNA fragments to provide a second DNA fragment pattern;

(e) comparing the first and second DNA fragment patterns; and (f) performing each of steps (a)–(e) with at least a second microsatellite region.

7. A method to aid in the determination of familial colon cancer (FCC) comprising the steps of:

comparing at least two microsatellite markers in a tumor tissue of a human to the at least two microsatellite markers in a normal tissue of the human;

classifying the tumor as an RER– phenotype tumor if less than two rearrangements are found in the microsatellite markers in the tumor tissue; wherein an RER– phenotype tumor indicates that the human does not have FCC.

8. The method of claim 7 further comprising:

providing a diagnosis that the human does not have FCC.

9. The method of claim 7 wherein the step of comparing is performed by the steps of:

(a) digesting DNA from a tumor of an individual with a restriction endonuclease to form tumor DNA fragments;

(b) separating said tumor DNA fragments;

(c) hybridizing said tumor DNA fragments to a microsatellite probe to provide a first hybridization pattern;

(d) digesting DNA from a normal tissue of the individual with the restriction endonuclease to form normal DNA fragments;

(e) separating said normal DNA fragments;

(f) hybridizing said normal DNA fragments to the microsatellite probe to provide a second hybridization pattern;

(g) comparing the first and second hybridization patterns;

(h) performing each of steps (a)–(g) with at least a second microsatellite probe.

10. The method of claim 7 wherein the step of comparing is performed by the steps of:

(a) amplifying a microsatellite region of DNA from a tumor of an individual to form tumor DNA fragments;

(b) separating said tumor DNA fragments to provide a first DNA fragment pattern;

(c) amplifying the microsatellite region of DNA from a normal tissue of the individual to form normal DNA fragments;

(d) separating said normal DNA fragments to provide a second DNA fragment pattern;

(e) comparing the first and second DNA fragments patterns; and (f) performing each of steps (a)–(e) with at least a second microsatellite region.

11. The method of claim 7 wherein the microsatellite marker is a dinucleotide or trinucleotide repeat marker.

12. The method of claim 8 wherein the step of comparing is performed by the steps of:

(a) digesting DNA from a tumor of an individual with a restriction endonuclease to form tumor DNA fragments;

(b) separating said tumor DNA fragments;

(c) hybridizing said tumor DNA fragments to a microsatellite probe to provide a first hybridization pattern;

(d) digesting DNA from a normal tissue of the individual with the restriction endonuclease to form normal DNA fragments;

(e) separating said normal DNA fragments;

(f) hybridizing said normal DNA fragments to the microsatellite probe to provide a second hybridization pattern;

(g) comparing the first and second hybridization patterns;

(h) performing each off steps (a)–(g) with at least a second microsatellite probe.

13. The method of claim 8 wherein the step of comparing is performed by the steps of:

(a) amplifying a microsatellite region of DNA from a tumor of an individual to form tumor DNA fragments;

(b) separating said tumor DNA fragments to provide a first DNA fragment pattern;

(c) amplifying the microsatellite region of DNA from a normal tissue of the individual to form normal DNA fragments;

(d) separating said normal DNA fragments to provide a second DNA fragment pattern;

(e) comparing the first and second DNA fragments patterns; and (f) performing each of steps (a)–(e) with at least a second microsatellite region.

14. The method of claim 8 wherein the microsatellite marker is a dinucleotide or trinucleotide repeat marker.

15. A method to aid in the determination of familial colon cancer (FCC) comprising the steps of:

comparing at least two simple repeated sequences in a tumor tissue of a human to the at least two simple repeated sequences in a normal tissue of the human;

classifying the tumor as a RER– phenotype tumor if less than two rearrangements are found in the simple repeated sequences in the tumor tissue; wherein an RER– phenotype tumor indicates that the human does not have FCC.

16. The method of claim 15 further comprising:

providing a diagnosis that the human does not have FCC.

17. The method of claim 15 wherein the step of comparing is performed by the steps of:

(a) digesting DNA from a tumor of an individual with a restriction endonuclease to form tumor DNA fragments;

(b) separating said tumor DNA fragments;

(c) hybridizing said tumor DNA fragments to a simple repeated sequence probe to provide a first hybridization pattern;

(d) digesting DNA from a normal tissue of the individual with the restriction endonuclease to form normal DNA fragments;

(e) separating said normal DNA fragments;

(f) hybridizing said normal DNA fragments to the simple repeated sequence probe to provide a second hybridization pattern;

(g) comparing the first and second hybridization patterns;

(h) performing each of steps (a)–(g) with at least a second simple repeated sequence probe.

18. The method of claim 15 wherein the step of comparing is performed by the steps of:

(a) amplifying a simple repeated sequence region of DNA from a tumor of an individual to form tumor DNA fragments;

(b) separating said tumor DNA fragments to provide a first DNA fragment pattern;

(c) amplifying the simple repeated sequence region of DNA from a normal tissue of the individual to form normal DNA fragments;

(d) separating said normal DNA fragments to provide a second DNA fragment pattern;

(e) comparing the first and second DNA fragments patterns, and (f) performing each of steps (a)–(e) with at least a second simple repeated sequence region.

19. The method of claim 15 wherein the simple repeated sequence is a dinucleotide or trinucleotide repeat marker.

20. The method of claim 16 wherein the step of comparing is performed by the steps of:

(a) digesting DNA from a tumor of an individual with a restriction endonuclease to form tumor DNA fragments;

(b) separating said tumor DNA fragments;

(c) hybridizing said tumor DNA fragments to a simple repeated sequence probe to provide a first hybridization pattern;

(d) digesting DNA from a normal tissue of the individual with the restriction endonuclease to form normal DNA fragments;

(e) separating said normal DNA fragments;

(f) hybridizing said normal DNA fragments to the simple repeated sequence probe to provide a second hybridization pattern;

(g) comparing the first and second hybridization patterns;

(h) performing each of steps (a)–(g) with at least a second simple repeated sequence probe.

21. The method of claim 16 wherein the step of comparing is performed by the steps of:

(a) amplifying the simple repeated sequence region of DNA from a tumor of an individual to form tumor DNA fragments;

(b) separating said tumor DNA fragments to provide a first DNA fragment pattern;

(c) amplifying the simple repeated sequence region of DNA from a normal tissue of the individual to form normal DNA fragments;

(d) separating said normal DNA fragments to provide a second DNA fragment pattern;

(e) comparing the first and second DNA fragments patterns, and (f) performing each of steps (a)–(e) with at least a second simple repeated sequence region.

22. The method of claim 16 wherein the simple repeated sequence is a dinucleotide or trinucleotide repeat marker.

23. The method of claim 7 wherein the tumor is classified as RER– if less than two of seven markers are found to be rearranged.

24. The method of claim 8 wherein the tumor is classified as RER– if less than two of seven markers are found to be rearranged.

25. The method of claim 15 wherein the tumor is classified as RER– if less than two of seven simple repeated sequences are found to be rearranged.

26. The method of claim 16 wherein the tumor is classified as RER– if less than two of seven simple repeated sequences are found to be rearranged.

* * * * *